United States Patent [19]
Mignot

[11] Patent Number: 5,297,552
[45] Date of Patent: Mar. 29, 1994

[54] PROCESS FOR MEASURING THE POSITION OF AT LEAST ONE MOBILE INTERFACE USING ULTRASOUND AND APPARATUS FOR CARRYING OUT SAID PROCESS

[75] Inventor: Jean-Pierre Mignot, Peseux, Switzerland

[73] Assignee: Asulab S.A., Bienne, Switzerland

[21] Appl. No.: 941,254

[22] Filed: Sep. 4, 1992

[30] Foreign Application Priority Data

Sep. 27, 1991 [CH] Switzerland ............... 02871/91

[51] Int. Cl.$^5$ ............................................. A61B 8/00
[52] U.S. Cl. ............................................. 128/661.04
[58] Field of Search ......... 128/660.01, 661.03–661.06, 128/661.09–661.10

[56] References Cited

U.S. PATENT DOCUMENTS

| | | | |
|---|---|---|---|
| 4,370,985 | 2/1983 | Takeichi et al. | 128/661.09 |
| 4,660,564 | 4/1987 | Benthin et al. | 128/661.04 X |
| 4,966,150 | 10/1990 | Etienne et al. | 128/661.04 |

FOREIGN PATENT DOCUMENTS

| | | |
|---|---|---|
| 337297 | 4/1989 | European Pat. Off. . |
| 356629 | 6/1989 | European Pat. Off. . |
| 0409054 | 4/1992 | European Pat. Off. . |
| 2853170 | 6/1980 | Fed. Rep. of Germany . |
| 2632733 | 12/1989 | France . |

OTHER PUBLICATIONS

Assessment of the True Pulse-Wave Velocity Over Physiological Pressure Range, IEEE vol. 12, No. 4, 1990, pp. 1817–1818.

Primary Examiner—Francis Jaworski
Attorney, Agent, or Firm—Griffin, Butler, Whisenhunt & Kurtossy

[57] ABSTRACT

A process for measuring the position of at least one mobile wall using ultrasound and an apparatus for carrying out this process are described.

The measuring process of the invention has an initialization phase during which the elemental echoes of an echo signal produced by the reflection of an ultrasonic impulse from mobile interfaces ($P_{o,1}$; $P_{o,2}$; $P_{o,3}$; $P_{o,4}$;) are processed, to determine the position of these interfaces in this echo signal and in which the temporal positions of the reference points ($Z_{o,1}$; $Z_{o,2}$) of the elemental echoes of a group of echo signals assimilated afterwards, are simultaneously tracked so as to ascertain the position of the interfaces in the most recent of the echo signals of this group, an assimilation phase in which the position of said interfaces is tracked and an organizational or processing stage for the memorized data.

The invention has applications in the medical field for measuring the interior diameter and thickness of the wall of a blood vessel as a function of time.

16 Claims, 6 Drawing Sheets

PROCESS FOR MEASURING THE POSITION OF AT LEAST ONE MOBILE INTERFACE USING ULTRASOUND AND APPARATUS FOR CARRYING OUT SAID PROCESS

FIELD OF THE INVENTION

The instant invention relates to a process for measuring the position of at least one mobile wall using ultrasound and an apparatus for carrying out this process.

The invention is useful whenever it is desired to monitor the change with time in the position of a mobile wall, in particular in the medical field. In the latter case, the invention may be employed to follow the change with time in the position of the interfaces of the anterior and posterior walls of a blood vessel to determine the changes in the inner diameter and in the thickness of the walls of a blood vessel as a function of time. It may also have applications in measuring the thickness of the corneal lens.

FIG. 1 illustrates diagrammatically the principle of measuring the displacement of at least one mobile wall. This figure shows an ultrasonic transducer 2 placed on the skin 4 of a subject opposite an artery 6 shown in transverse section. The transducer 2 is controlled by an electronic circuit to transmit an impulse of an ultrasonic wave 8 and to receive the echoes resulting from reflection of this impulse from the artery-tissue or artery-blood interfaces. Depending on the frequency of the ultrasonic transducer it is possible to detect four distinct echoes 10, 12, 14, 16 or only two echoes corresponding respectively to a combination of the echoes 10 and 12 and to a combination of the echoes 14 and 16.

Knowledge of the temporal position of each interface as well as the speed of propagation of sound in the blood and the tissues makes it possible, by measuring the interval, to determine the change as a function of time of the inner diameter and of the thickness of the anterior and posterior walls of the blood vessel 6.

FIG. 1 is a schematic diagram. In practice, the echoes $E_{ant}$ and $E_{post}$ originating from the anterior and posterior walls of the blood vessel are not so simple, but have a much more complex shape as shown in FIG. 2. This deformation results from the fact that the ultrasonic signal passes through different kinds of tissues and from the fact that the interface between the wall of a blood vessel and the surrounding tissue is not clearly defined.

The position of an interface, especially in the medical field, can therefore not be inferred directly and automatically from the shape of the echo signal.

DESCRIPTION OF THE PRIOR ART

Various ultrasonic methods are known for detecting the position of a moving interface.

A first method consists in processing the echo signal to suppress noise, only keeping in practice that part of the signal resulting from the reflection of the ultrasonic signal from the interface. However the disadvantage of this method is that it cannot be carried out on a real time basis. Using conventional calculation means, processing of the echo signal requires of the order of 0.1 to 5 seconds whereas, with a repeat frequency of 100 Hz, the time available for the real time processing of an echo signal is of the order of 0.01 seconds.

It is therefore necessary to proceed in two stages: firstly to store the group of echo signals to be studied in a memory in real time and, secondly, to process these echo signals. It will be understood that this method has three disadvantages namely the need to have a large amount of memory, the time taken to process the echo signals and the absence of real time checks of the data being collected.

In a second known method, the position of the interface is determined manually. The user transmits the echo signal on an oscilloscope or any other display means and chooses a specific point of the echo signal on which the echo tracker has to lock. The disadvantages of the first method are thereby overcome. On the other hand, this method requires great experience on the part of the user to determine the specific point of the echo which corresponds to the position of the interface. In practice, the user chooses either the impulse of greatest amplitude, or the central impulse of the echo signal. There is, however, nothing to ensure that the point chosen actually corresponds to the position of the interface. This second method makes it possible, at best, to determine the displacement of a relatively rigid wall, but does not make it possible to measure exactly the internal diameter of a blood vessel or the thickness of the wall thereof.

OBJECTS OF THE INVENTION

It is an object of the invention to overcome the disadvantages of these known methods.

BRIEF SUMMARY OF THE INVENTION

Essentially, the instant invention consists of an initialising phase in which a first echo signal is processed to determine the position of at least one interface in this first echo signal and in which the position at a given time of a group of subsequently received echo signals is simultaneously tracked in such a way as to ascertain the position of the interface within the most recent of the echo signals of this group, which occurs after determination of the position of said interface in said first echo signal, and an assimilation phase in which the position of said interface is analysed.

More precisely it is an object of the invention to provide a process for measuring the position of at least one mobile interface using ultrasound consisting in emitting an ultrasonic interrogating impulse at a repeat frequency $F_r$ towards said interface in cyclical manner, and in receiving an echo signal having at least one elemental echo, this elemental echo resulting from the reflection of said ultrasonic impulse from said interface, this process having:

an initialization stage consisting of selecting a reference point in each elemental echo of a group of elemental echoes of the echo signal of a first ultrasonic impulse; processing said echo signal of said first ultrasonic impulse to determine, from each of said elemental echoes, the position at a given time of the interface producing this elemental echo, calculating for each of said elemental echoes of the echo signal of said first ultrasonic impulse, the temporal interval between the position of the reference point of said elemental echo and the temporal position of the interface obtained by said processing; and simultaneously during the processing and calculation, observing the change in position with time of the reference points of each of said elemental echoes of a first group of echo signals from ultrasonic impulses subsequent to said first ultrasonic impulse;

an assimilation phase consisting in observing and memorizing the temporal position of the interface corresponding to each of said elemental echoes of a second group of echo signals received subsequent to said echo signal of said first ultrasonic impulse; and a processing stage of the data memorized during the assimilation phase.

It is also an object of the invention to provide an apparatus for carrying out this process.

BRIEF DESCRIPTION OF THE DRAWINGS

The characteristics and advantages of the invention may be better seen from the following description which is given solely as a non-limiting illustration, with reference to the appended drawings, in which.

DETAILED DESCRIPTION OF THE INVENTION

Figure 1:
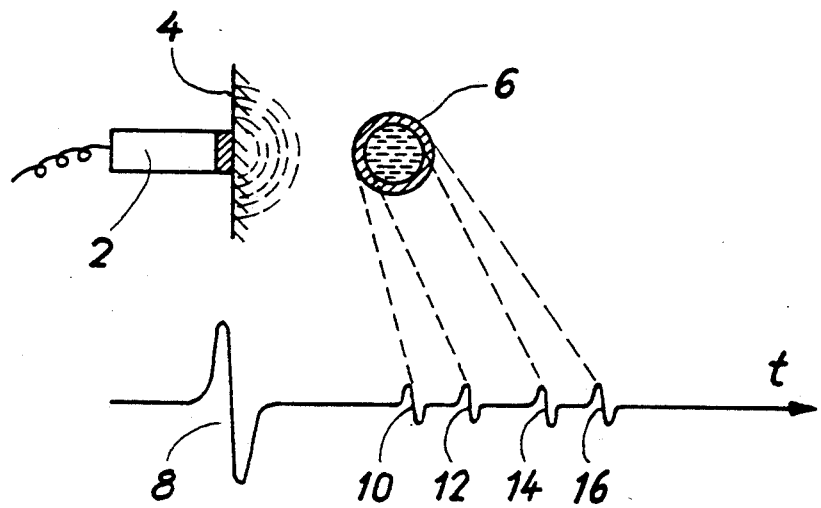
FIG. 1, already described, illustrates the principle of ultrasonic measurement of the position of the interfaces of the anterior and posterior walls of a blood vessel, FIG. 2, already described, illustrates the temporal shape of an elemental echo produced by the interface between the tissue and the wall of a blood vessel.
Figure 2:
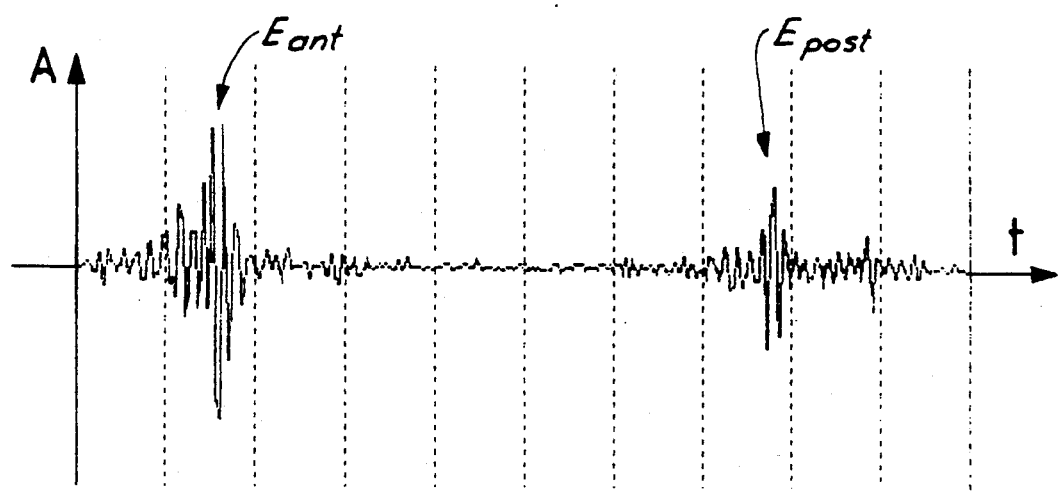
Figure 3:
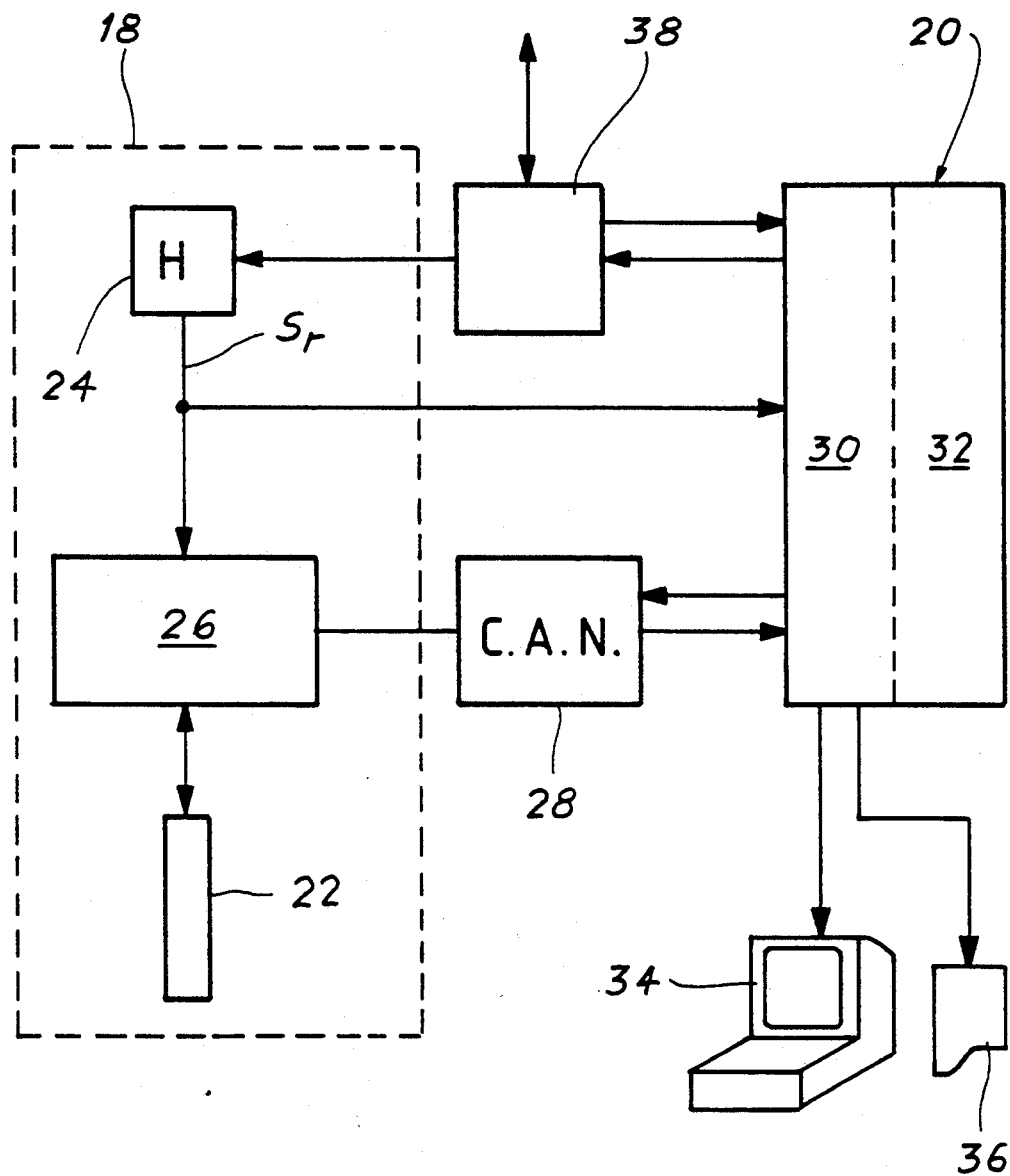
FIG. 3 shows diagrammatically an apparatus for carrying out the process of the invention.

FIG. 3 shows in diagrammatic form an apparatus for carrying out the process of the invention. This apparatus mainly comprises an ultrasonic transducer 18 and a processing device 20. The ultrasonic transducer 18 has an ultrasonic probe 22 for transmitting an ultrasonic signal and receiving the echoes resulting from the reflection of this ultrasonic wave, a control circuit 26 for controlling the ultrasonic wave 22 and a clock 24. The latter delivers to the control circuit 26 a signal $S_r$ defining the frequency of repetition $F_r$ of the interrogation signal emitted by the ultrasonic probe.

The control circuit comprises a transmitter circuit delivering an electrical impulse which is transformed by the ultrasonic probe 22 into a corresponding ultrasonic signal, and a receiving circuit receiving the electrical signal delivered by the ultrasonic probe corresponding to the ultrasonic echo signal received by the ultrasonic probe. The control circuit and the ultrasonic probe are of a conventional type. The central frequency of the ultrasonic impulse is chosen as a function of the intended application. It is, for example, from 2 to 20 MHz.

The electrical echo signal delivered by the control circuit is received by the processing device 20 through an analog-digital converter 28. It is possible to use for this purpose a product of the type STR 8100 from SONIX Inc (Springfield, Va., USA) which is an analog-digital 8 bit converter capable of processing up to $10^8$ calculations/second. The calculating device 20 has an echo tracker which is used in conventional manner to track the temporal position of each elemental echo of a group of elemental echoes of the echo signal in relation to the ultrasonic signal transmitted. This position, that is ultimately the delay in each elemental echo signal on the ultrasonic impulse transmitted, varies with the distance between the ultrasonic probe and the mobile interfaces from which the ultrasonic impulse is reflected. To carry out this tracking, the echo tracker of the processing device receives the clock signal produced by the clock 24 and delivers to the analog-digital converter 28 a delay signal to start digitalization of the echo signal at a suitable moment. The echo tracker is preferably of the detection in extremum type (positive or negative) of the digitized echo signal. This extremum is not the correct value for assessing the movement of the mobile walls since the distance between two sampling points is equal to $c/(2.f)$ where $c=1500$ m/s is the speed of ultrasonic waves in the medium and $f=100$ MHz is the sampling frequency. It is only possible to follow the displacement of the echo roughly.

Alternatively, the echo tracker could be of the crossover detection type such as described in EP-A-337 297 and EP-A-356 629.

The processing device 20 implements the measuring process of the invention. To do this it has, as main components, processing means 30 and memorizing means 32. This processing means is advantageously a personal computer with an 80×86 or 680×0 type processor. Various peripheral apparatus may be added, such as display means 4, printing means 36 and an input-output circuit 38. This latter may in particular be connected to the clock 24 to control the frequency of repetition $F_r$ of the clock signal from the calculating device. It may also serve to synchronize other measuring equipment such as a sphygmomanometer, a plethysmograph or a Doppler sensor in order to measure the blood pressure and blood rate.

The apparatus may comprise a second ultrasonic sensor and a second control circuit, this latter receiving the signal $S_r$ of the clock 24. In this case, the analog-digital converter 28 processes the echo signals received by the two sensors alternately. Since these echo signals are synchronous, it is possible to deduce the pulse-wave velocity in known manner therefrom. Reference is made notably to the article "Assessment of the true pulse-wave velocity over the physiological pressure range" by Y. Tardy et al. published in Proceedings of the 12th annual international conference of the IEEE engineering in medicine and biology society, Philadelphia, Pa., Nov. 14, 1990.

One embodiment of the process of measurement using ultrasound of the invention will now be described with reference to FIGS. 4A to 9.

Before beginning measurements per se, the user selects the parameters of the apparatus, such as the repetition frequency $F_r$ and the sensor, i.e. the central frequency of the ultrasonic impulse. These parameters could also be selected automatically by the processing device 20 as a function of the application chosen by the user. By way of example, in the event of measuring the internal diameter and the thickness of the blood vessel wall, the frequency $F_r$ is of the order of 2000 Hz and the central frequency of the ultrasonic impulse of the order of 10 MHz for measurement of the radial artery and of the order of 4 MHz for measurement of the carotid. The duration of the delay transmitted to the analog-digital converter 28 of the apparatus is also adjusted, manually or automatically, so that the echo tracker tracks each echo correctly. From then on the echo tracker works automatically. The user can then proceed to measure the position of the interfaces of the blood vessel by carrying out the measurement process of the invention using the processing device 20.

This measurement process can be divided into three stages, namely an initialization stage (A), an assimilation stage (B) and a processing stage (C).

The initialization stage (A) consists in determining the temporal position of the mobile interfaces causing each elemental echo of a first echo signal. For this purpose the echo signal $E_0$ produced by an ultrasonic impulse is digitized by the analog-digital converter 28 and the elemental echoes $Ee_{0,1}$, $Ee_{0,2}$, ..., $Ee_{0,n}$ each corresponding to the reflection of the ultrasonic impulse from one mobile wall, are stored in the memory means 32 (operation 40). In practice those parts of the echo signal are memorized which correspond to the echoes of the anterior wall $E_{ant,0}$ and posterior $E_{post,0}$ of the blood vessel. Each of these echoes can have one or several elemental echoes which will be displayed after processing of the signal. In the case of a blood vessel, each ultrasonic impulse normally produces four elemental echoes, two of these elemental echoes being produced by the anterior wall while the other two elemental echoes are produced by the posterior wall.

Figure 6:
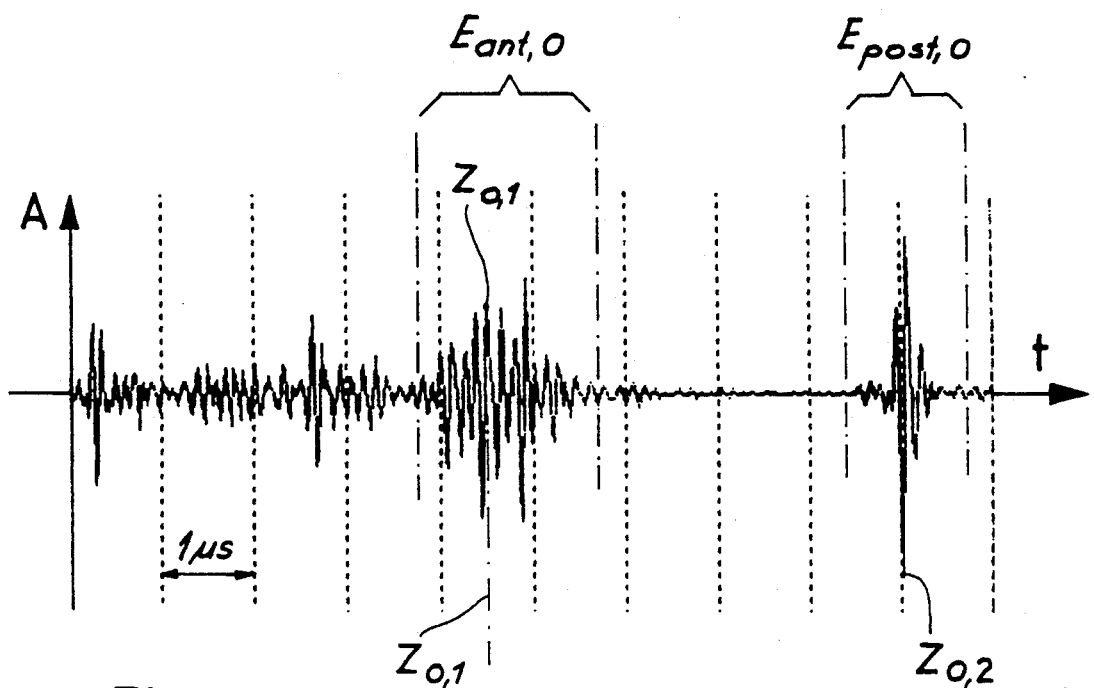
FIGS. 6 to 9 are organizational diagrams of echo signals illustrating the working of the process of the invention.

The processing device 20 then selects from each elemental echo a reference point designed to identify the temporal position of each elemental echo (operation 42 and FIG. 6). These reference points $Z_{0,i}$, or $0 \leq i \leq m$, are preferably a prominent point of each elemental echo, such as the impulse of greatest amplitude or the central impulse of the elemental echo. When the two elemental echoes move in the same manner as a function of time it is possible to mark the position in time of these two elemental echoes using a single reference point. This is the case in particular of the elemental echoes produced respectively by the anterior wall and the posterior wall of a blood vessel. It is therefore possible in this case to choose a single reference point $Z_{0,1}$ and $Z_{0,2}$ respectively for the group of elemental echoes of the echoes $E_{ant,0}$ and $E_{post,0}$ respectively, as shown in FIGS. 6 and 7.

Figure 4:
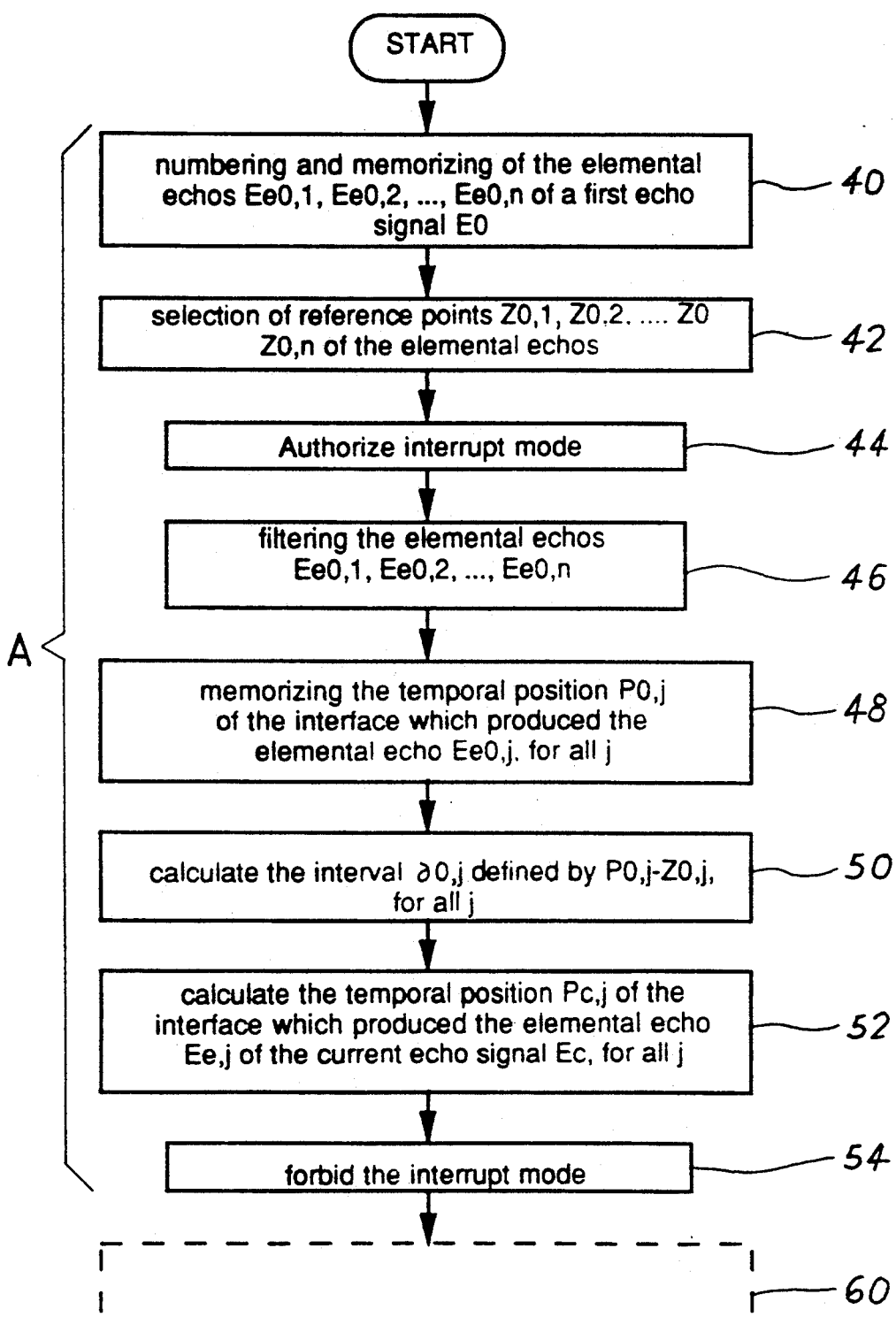
FIGS. 4a and 4b are organizational diagrams of the main process of the invention and FIG. 5 is an organizational chart of the interrupt process.
Figure 4B:
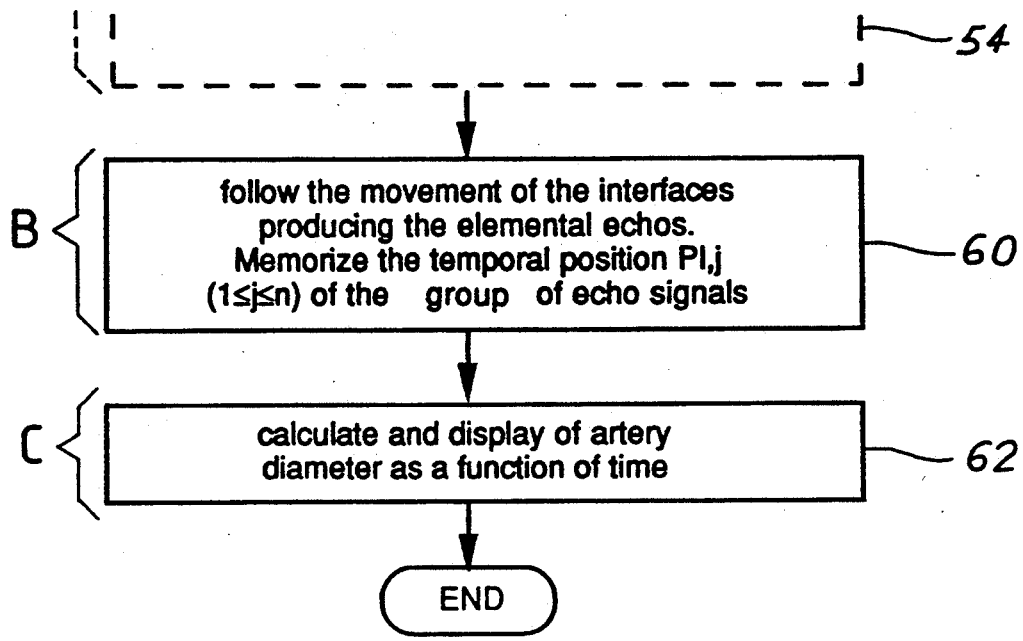
Figure 5:
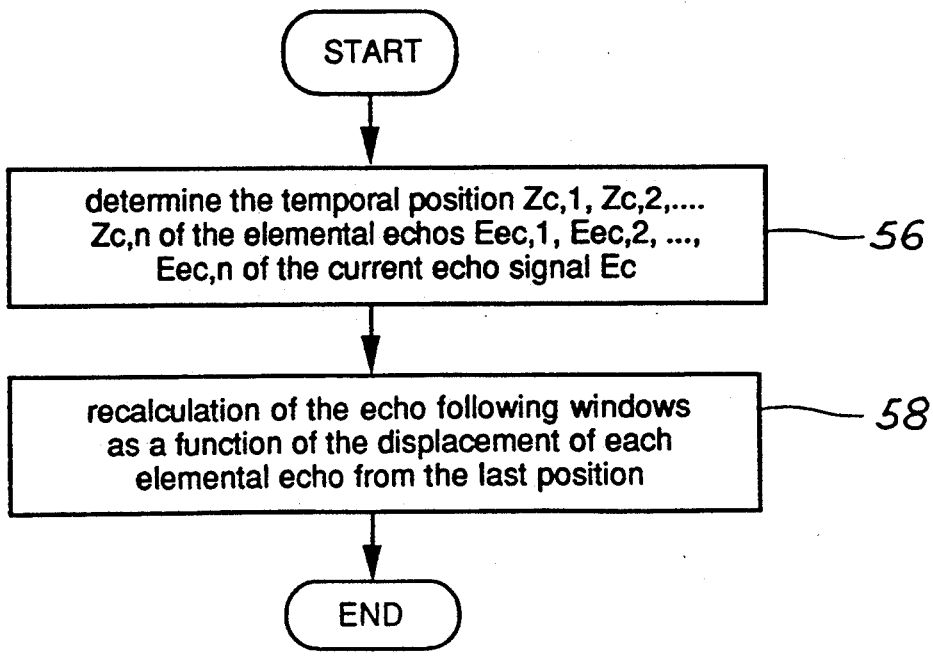

The temporal position of the mobile interface corresponding to each elemental echo of a group of elemental echoes selected in said first echo signal is then determined from the digitized and memorized elemental echo signal. This determination consists in processing the digitized signal to eliminate the noise therefrom and thus extract the resultant impulse of the reflection of the ultrasonic impulse from the mobile interface. During this processing, the duration of which is of the order of a few seconds with the current means of processing, it is necessary to continue tracking the position of the elemental echoes. This necessitates use of calculation means capable of carrying out these two tasks at the same time or of proceeding by periodic interruption of the processing to follow the displacement of the elemental echoes. It is this second method which is shown in FIGS. 4 and 5.

Different processing methods are known to determine the position of a mobile interface as from the echo produced by the reflection of an ultrasonic impulse on this mobile interface. By way of example it is possible to use the processing method described in document EP-A-409054.

Figure 7:
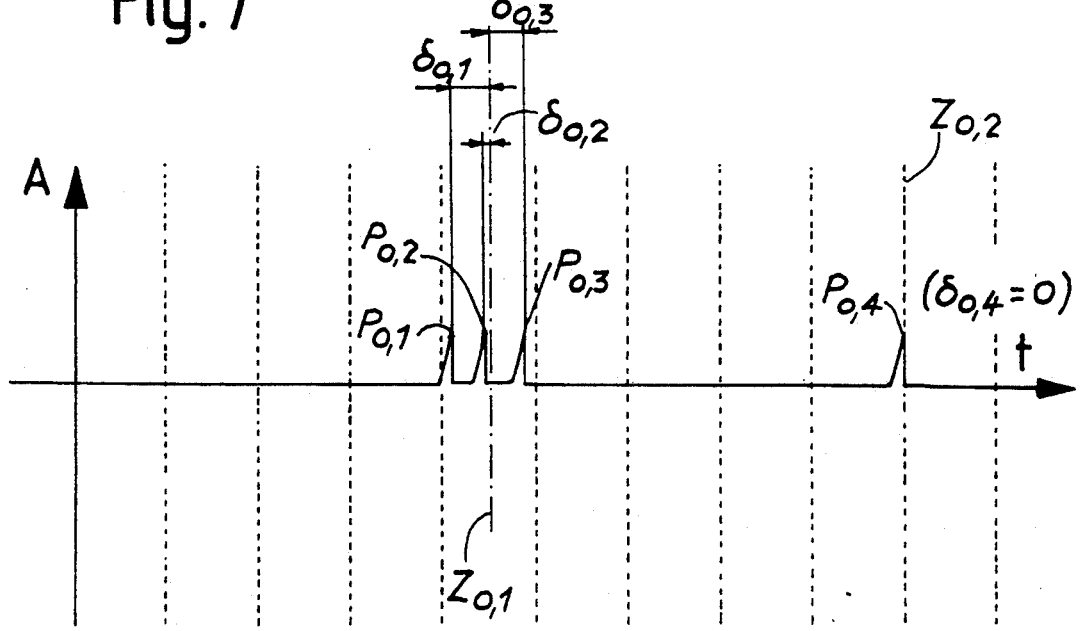

The processing operation 46 makes it possible to obtain from each elemental echo an impulse which marks the temporal position $P_{0,j}$ of the corresponding mobile interface (see FIG. 7). In the example shown, three interfaces have been detected in the echo $E_{ant,0}$ of the anterior wall of the blood vessel (these are respectively the tissue-vessel interface, an internal interface of the vessel and the vessel-blood interface) whereas a single interface is visible in the echo $E_{post,0}$ of the posterior wall of the blood vessel. The calculating device then proceeds to memorize these temporal positions $P_{0,j}$ for each elemental echo $Ee_{0,j}$ of the echo $E_0$ (operation 48) and calculates the temporal interval $\delta_{0,j}$ between the temporal position of the reference point $Z_{0,i}$ and the temporal position $P_{0,j}$ of the interface (operation 50). This interval remains the same for the successive elemental echoes produced by a same mobile interface in response to successive ultrasonic impulses. It will be noted that the reference point $Z_{0,1}$ chosen to follow the given position of the echo $E_{ant,0}$ does not correspond to any mobile interface, whereas the reference point $Z_{0,2}$ chosen to follow the given position of the echo $E_{post,0}$ corresponds, by chance, to the position of the mobile interface detected.

Knowledge of the temporal interval for each elemental echo makes it possible to determine, in the unfiltered elemental echo signal, the impulse marking the position of the mobile interface as from the position of the reference point. This makes it possible to relocate the echo tracker on the corresponding impulse at the effective position of each mobile interface (operation 52). It is also possible to continue to lock the echo tracker on the reference point of each elemental echo, it being understood that the position of each mobile interface can be deduced therefrom immediately with the temporal interval.

During operations 46 to 52, the processing effected by the calculating device has to be periodically interrupted to permit tracking of the displacement of the elemental echoes. Operations 44 and 54 place the calculation device in AUTHORIZE INTERRUPT mode and FORBID INTERRUPT mode respectively.

Processing is interrupted at a frequency that is sufficient to ensure tracking of the echo. This interrupt frequency $F_i$ depends on the maximum speed of displacement of the walls and of the frequency $F_r$ of the ultrasonic interrogation impulse. It is also necessary for this interrupt frequency $F_i$ not to be too high so that processing is not interrupted too often. In the case of measurement in a blood vessel, an interrupt frequency $F_i$ of a few hundred hertz may be used. The interrupt signal may advantageously be obtained by division of the repetition signal delivered by the clock 24. The echo tracker then receives the echo signal of an ultrasonic impulse on K, where K is the ratio between the repetition frequency $F_r$ and the interrupt frequency $F_i$.

Figure 8:
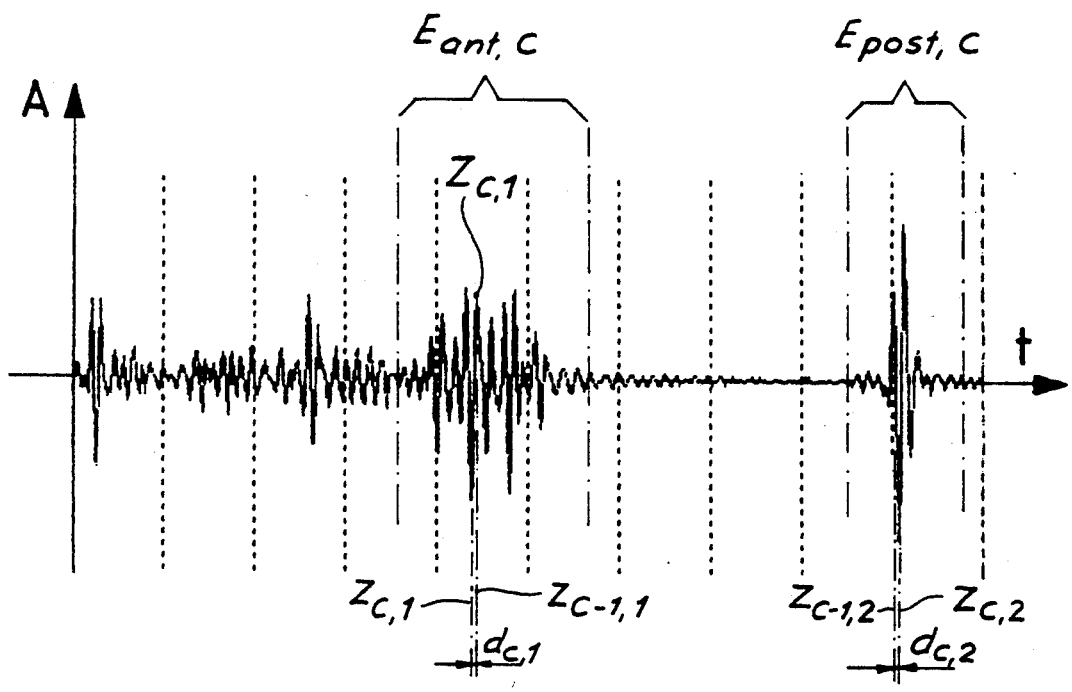

The interrupt processing comprises an operation 56 for determining the temporal position of the reference points $Z_{c,i}$ of the elemental echoes $Ee_{c,j}$ of the first echo signal $E_c$ received after the interrupt signal or, what comes to the same thing, of the measurement of the displacement of each reference point between the echo signal $E_c$ received after the interrupt signal and the preceding echo signal $E_{c-1}$, and an operation 58 of recalculating of the echo following windows as a function of the displacement $d_{c,1} d_{c,2}$, of each elemental echo since the last interrupt signal (see FIG. 8). Since these operations are conventional in the field of measuring the position of a mobile wall using ultrasound, they need not be described in greater detail here.

The initialization stage which has just been described is followed by the assembly stage (B). This stage comprises an operation 60 consisting of tracking the temporal position of each mobile interface of said group of elemental echoes selected in said first echo signal. To do this, the positions $P_1$ indicated by the echo tracker are noted and a quadratic interpolation is then carried out with the neighbouring sampling points. This gives an accuracy of the order of 0.5 m (with a sampling frequency of 100 MHz). These positions are memorized for a given group of ultrasonic impulses. The assembly is preferably carried out on a group of ultrasonic impulses received after the end of the initialization stage. Nonetheless it is possible to choose a different group of ultrasonic impulses, and for example to retain for the assimilation stage some or all of the ultrasonic impulses memorized in response to the interrupt signal during the initialization stage.

In conventional manner, to increase the resolution, it is advantageous to assemble the ultrasonic waves at a first frequency (in practice, this first frequency is simply the frequency of repetition $F_r$) and only to memorize the ultrasonic waves, or at least the position of each mobile interface, at a second frequency, being a submultiple of the first frequency, the memorized position of each mobile interface being equal to the mean of the positions recorded during the p last ultrasonic waves, where p is the ratio between the first frequency and the second frequency. The accuracy of the position of the interfaces is thus increased by a factor $\sqrt{p}$.

Figure 9:
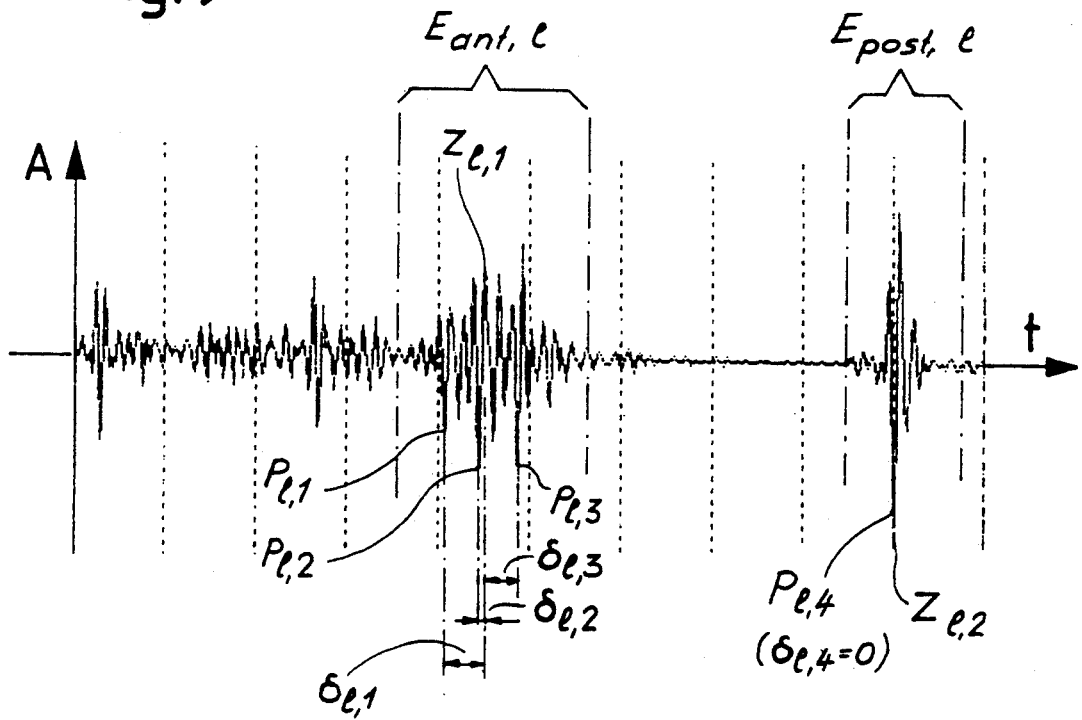

With regard to memorizing the data relating to each elemental echo $Ee_{1,j}$, it is possible to select the temporal position of the mobile interface $P_{1,j}$ or the temporal position of the reference point $Z_{1,i}$, the interval between these two positions being, for each elemental echo, constant and equal to the distance $\delta_{0,j}$ determined during operation 50 (see FIG. 9). Similarly, as shown hereinabove with reference to operation 52, the echo tracker can be locked either on the position of the reference points or on the position of the mobile interfaces.

The volume of memorized data depends on the available memory in the processing device 20 and on the time accorded to the assembly stage.

All that remains to be done is to process the memorized data according to the user's needs (operation 62). This processing (C) can consist in calculating and visualizing the internal diameter and thickness of the wall of the blood vessel as a function of time, and in deducing other physiological parameters such as the compliance of the blood vessel by combining the data relating to the diameter with the data relating to the blood flow obtained using different measurement apparatus, for example data on blood pressure at the site of the measurement effected in the context of the instant invention.

I claim:

1. A process for measuring the temporal evolution of the position of a mobile interface of an inhomogeneous body wherein ultrasonic impulses are transmitted at a repetition frequency $F_r$ in said inhomogeneous body towards said mobile interface, each ultrasonic impulse generating an echo signal having an elemental echo comprising a plurality of impulses resulting from the reflection of such ultrasonic impulse from a region near to and including said mobile interface, said process comprising an initialization step wherein:

a first echo signal is detected and the said elemental echo is located in said first echo signal, a reference point is selected on the elemental echo of said first echo signal, said elemental echo of said first echo signal is processed to determine accurately the position of said mobile interface in said first elemental echo and simultaneously the temporal evolution of the position of said reference point is tracked in a first group of echo signals detected subsequent to said first echo signal;

said process further comprising a measurement step following said initialization step wherein the temporal evolution of the determined position of said mobile interface is tracked in a second group of echo signals following immediately said first group of echo signals.

2. A process according to claim 1, wherein the impulse of the largest amplitude of said elemental echo is selected as the reference point of this elemental echo.

3. A process according to claim 1, wherein the central impulse of said elemental echo is selected as the reference point of this elemental echo.

4. A process according to claim 1, wherein the group of echo signals tracked during the initialization step is a precise sub-group of the whole group of echo signals received at the frequency $F_r$.

5. A process according to claim 1 wherein said mobile interface corresponds to an external or internal interface of an anterior or posterior wall of a blood vessel.

6. A process according to claim 1, wherein simultaneous temporal evolutions of positions of a plurality of interfaces are determined.

7. An apparatus, for measuring the temporal evolution of the position of at least one mobile interface of a inhomogeneous body for carrying out the process according to claim 1, comprising an ultrasonic transducer to emit towards said at least one interface ultrasonic impulses at a repetition frequency $F_r$ and to detect echo signals resulting from the reflection of said ultrasonic impulses in said inhomogeneous body, said apparatus further comprising processing means for carrying out said initialization and measurement steps.

8. An apparatus according to claim 7 wherein the processing means have an interrupt input receiving an interrupt signal from an interrupt circuit included in said apparatus, the processing means then interrupting the operation in process to memorize the temporal position of said reference points of each of said elemental echoes of the echo signal received immediately after said interruption.

9. An apparatus according to claim 8, wherein said interrupt circuit comprises a clock, for producing a signal having a frequency which is a sub-multiple of the repetition frequency $F_r$.

10. A process for measuring the temporal evolution of the position of a mobile interface of an inhomogeneous body wherein ultrasonic impulses are transmitted at a repetition frequency $F_r$ in said inhomogeneous body towards said mobile interface, each ultrasonic impulse generating an echo signal having an elemental echo comprising a plurality of impulses resulting from the reflection of such ultrasonic impulse from a region near to and including said mobile interface, said process comprising an initialization step wherein:

a first echo signal is detected and the elemental echo is located in said first echo signal, a reference point is selected on said elemental echo, said elemental echo of said first echo signal is processed to determine accurately the position of said mobile interface in said first elemental echo and simultaneously the temporal evolution of the position of said reference point is tracked in a first group of echo signals detected subsequent to said first echo signal;

the position difference between said reference point and said mobile interface is calculated;

said process further comprising a measurement step wherein the temporal evolution of the reference point is tracked in a second group of echo signals detected subsequent to said first echo signal, the position of said reference point in each echo signal of said second group being memorized, the temporal evolution of said mobile interface in said second group of echo signals being calculated after said initialization step.

11. A process according to claim 10, wherein at least one part of the echo signals of the second group is composed of echo signals of the first group.

12. A process according to claim 10 wherein said mobile interface corresponds to an external or internal interface of an anterior or posterior wall of a blood vessel.

13. A process according to claim 10, wherein simultaneous temporal evolution of positions of a plurality of interfaces are determined.

14. An apparatus, for measuring the temporal evolution of the position of at least one mobile interface of a inhomogeneous body for carrying out the process according to claim 10 comprising an ultrasonic transducer to emit towards said at least one interface ultrasonic impulses at a repetition frequency $F_r$ and to detect echo signals resulting from the reflection of said ultrasonic impulses in said inhomogeneous body, said apparatus further comprising processing means for carrying out said initialization and measurement steps.

15. An apparatus according to claim 14 wherein the processing means have an interrupt input receiving an interrupt signal from an interrupt circuit included in said apparatus, the processing means then interrupting the operation in process to memorize the temporal position of said reference points of each of said elemental echoes of the echo signal received immediately after said interruption.

16. An apparatus according to claim 15, wherein said interrupt circuit comprises a clock, for producing a signal having a frequency which is a sub-multiple of the repetition frequency $F_r$.

* * * * *